(12) United States Patent
Hale et al.

(10) Patent No.: US 6,335,756 B1
(45) Date of Patent: Jan. 1, 2002

(54) MINIATURE VIDEOPROBE HOCKEY STICK DELIVERY SYSTEM

(75) Inventors: Lester R. Hale, Scotia; Kyle M. McMurry, Queensbury, both of NY (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 0 days.

(21) Appl. No.: 09/099,336

(22) Filed: Jun. 18, 1998

(51) Int. Cl.[7] .................................................. H04N 7/18
(52) U.S. Cl. ........................................ 348/82; 348/83
(58) Field of Search ............................. 348/82, 83, 84, 348/85

(56) References Cited

U.S. PATENT DOCUMENTS

| | | | | |
|---|---|---|---|---|
| 5,144,848 A | * | 9/1992 | Uenishi et al. ................ | 348/82 |
| 5,604,532 A | * | 2/1997 | Tillmanns ..................... | 348/84 |
| 5,633,675 A | * | 5/1997 | Danna et al. .................. | 348/85 |
| 5,689,734 A | * | 11/1997 | Bauer et al. ................... | 348/82 |
| 5,739,845 A | * | 4/1998 | Hansford et al. .............. | 348/83 |
| 5,790,185 A | * | 8/1998 | Auzerais et al. .............. | 348/84 |

* cited by examiner

*Primary Examiner*—Andy Rao
(74) *Attorney, Agent, or Firm*—John T. Lucas; Virginia B. Caress; Paul A. Gottlieb

(57) ABSTRACT

The present invention is a miniature videoprobe system having a probe termination box, a strong back, and a videoprobe housing. The videoprobe system is able to obtain images from a restricted space at least as small as 0.125" while producing a high quality image. The strong back has a hockey stick shape with the probe termination box connecting to the top of the handle-like portion of the hockey stick and the videoprobe housing attaching to the opposite end or nose of the hockey stick shape. The videoprobe housing has a roughly arrowhead shape with two thin steel plates sandwiching the internal components there between. The internal components are connected in series to allow for a minor dimension of the videoprobe housing of 0.110". The internal components include an optics train, a CCD chip, and an electronics package. An electrical signal is transmitted from the electronics package through wiring within an internal channel of the strong back to the probe termination box. The strong back has milled into it multiple internal channels for facilitating the transfer of information, items, or devices between the probe termination box and the videoprobe housing.

9 Claims, 4 Drawing Sheets

MINIATURE VIDEOPROBE HOCKEY STICK DELIVERY SYSTEM

FIELD OF THE INVENTION

This invention generally relates to visual videoprobe equipment. In particular, this invention relates to a miniaturized videoprobe and videoprobe apparatus that is insertable into small spaces where previously, only fiberscope equipment was insertable.

BACKGROUND OF THE INVENTION

Up to now, inspections of small restricted spaces and areas have been accomplished with flexible fiberscopes. The fiberscope technology relies on transmitting light through approximately 15 feet of a fiber-optic light guide, illuminating an object at the end of the fiberscope, receiving the light reflected back from the object, and transmitting the image back through the approximately 15 feet of fiber-optics to a charge couple device (CCD) chip located in a video camera. Such fiberscope arrangements have the disadvantage that information is lost during transmission of the reflected image back to the CCD chip in the camera body, thereby reducing the quality of the pictorial information received by the CCD chip.

Videoprobes also are common place in the prior art. Due to their size and configuration, prior art videoprobes have been unable to enter the same small, restricted spaces as fiberscopes. The prior art videoprobes typically have a circular cross-section with the CCD and accompanying circuitry on the front face. The smallest commercially available videoprobe is approximately 0.25" in cross-section. Videoprobes miniaturized to 0.110" requirements become overly fragile and easily damaged.

However, videoprobes still have a distinct advantage over fiberscopes by their placement of the CCD at the end of the device, adjacent the object being viewed. The CCD chip in the videoprobes then provides an electrical signal output representing the viewed image. This signal is transmitted back to a signal processor, which is approximately 15 feet removed from the CCD chip. The signal processor provides an NTSC TV signal. The overall arrangement in a videoprobe significantly reduces image transmission losses and allows use of an improved optic lens train which results in an improved field of view, focal ranges, depth of view, and image resolution.

SUMMARY OF THE INVENTION

The present invention overcomes image loss characteristics of fiberscopes by providing a miniaturized videoprobe, and videoprobe apparatus. The present invention overcomes fragility in, and strengthens a miniaturized videoprobe by incorporating a noncircular, circular, generally rectangular cross-section which differs from the generally circular shape of prior art videoprobe assemblies. The present invention places the CCD and accompanying circuity along a linear axis perpendicular to a front face of the videoprobe. The present invention is able to enter spaces as small as 0.125" that up to now were not accessible by prior art videoprobes.

A preferred embodiment of the present invention is a miniature videoprobe apparatus comprised of a Lexan (a registered trademark of General Electric Co.) plastic delivery tool strong back fabricated in the general shape of a hockey stick. The end of the hockey stick structure has a termination box with an umbilical connection to a videoprobe light supply and image signal processor. The other end of the hockey stick houses videoprobe electrical components and an optics train sandwiched between two thin stainless steel machined pieces. Within the hockey stick encasement, milled channels down the length of the stick pass fiber-optic light guides and image signal output wiring from the CCD chip electronics package. A preferred embodiment also has two additional utility or auxiliary channels to allow material sampling and nitrogen drying of areas of interest investigated by the videoprobe. The utility channels provide means for insertion of a fiberscope to provide a second image in addition to the one from the CCD chip.

The key advantages of this invention are related to the improved images now available from areas previously accessible only to fiberscopes. The image quality is significantly better, automatic focus eliminates manual focusing, the field depth is much improved, and the field of view is larger with the focal range being longer. The videoprobe is carried within the delivery tool to ensure that the orientation of the picture on the monitor is known as compared to a circular fiberscope whose alignment needs to be verified and frequently reoriented.

The present invention has possible application in jet engine visual exams, boiler tube inspections, medical invasive procedures, and checking the internal passages of complicated machine part castings. There is also potential for use by other U.S. Government projects that have inspection requirements for small internal areas requiring high quality resolution.

DETAILED DESCRIPTION OF THE PREFERRED EMBODIMENTS

Figure 1:
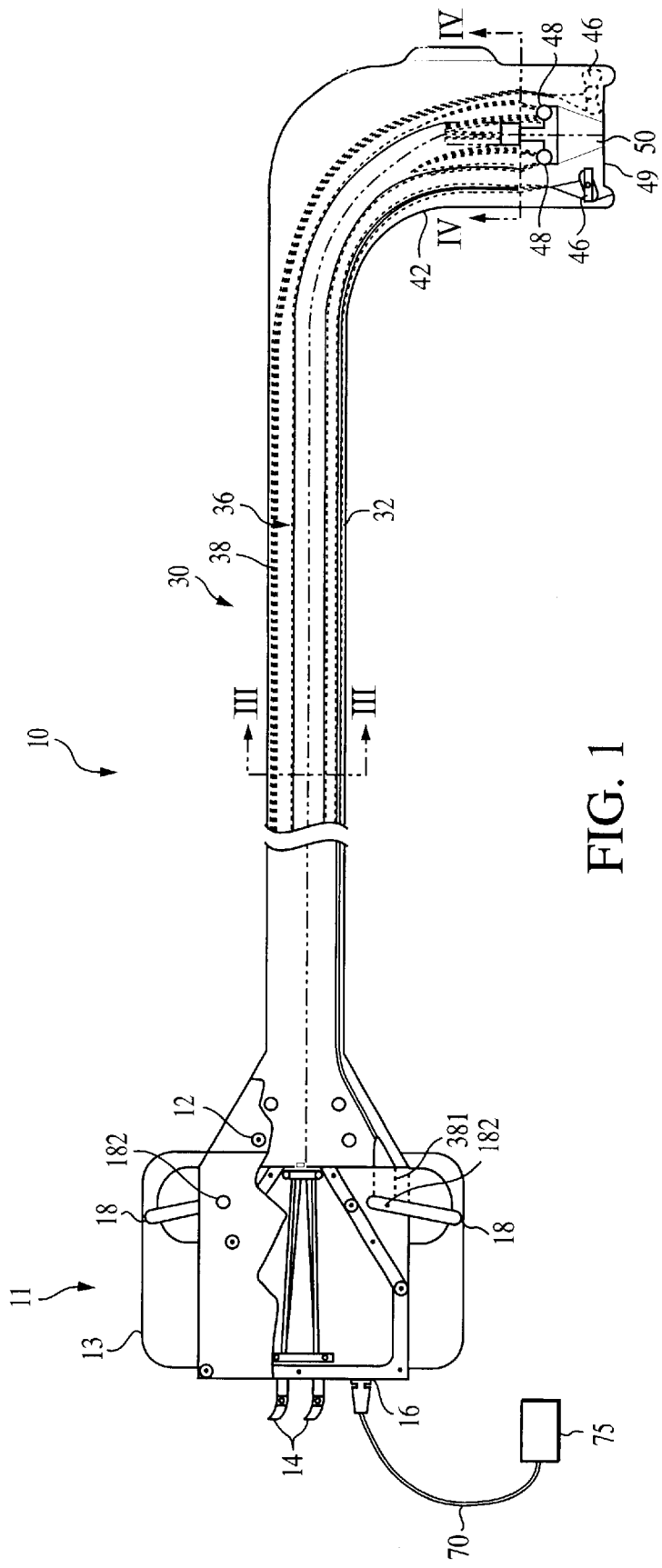
FIG. 1 is a partially cut-away plan view of a videoprobe apparatus in accordance with the present invention.
Figure 6:
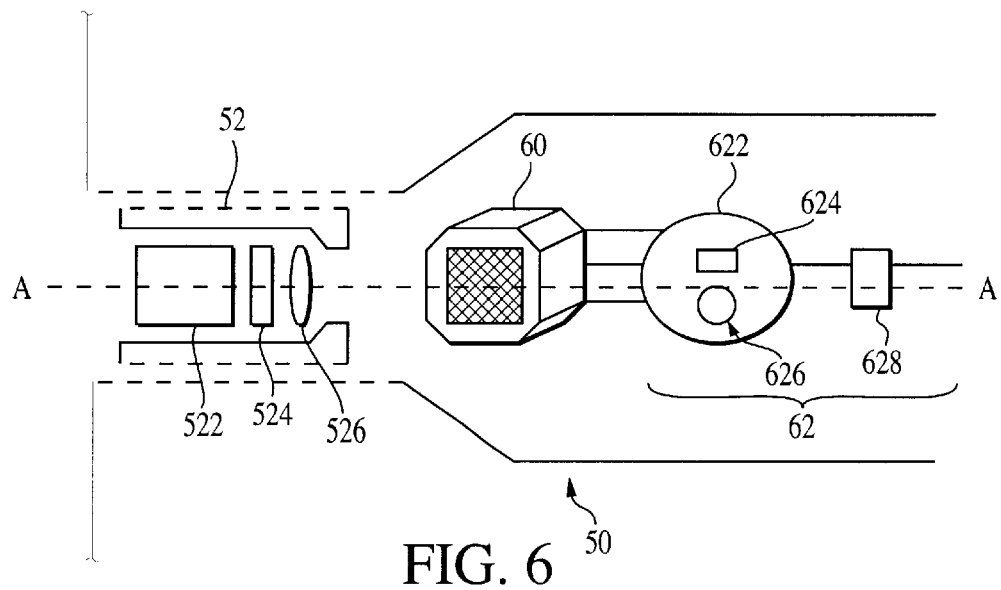
FIG. 6 is a block-diagram view showing of the imagery components of the videoprobe of FIG. 5.

A preferred miniature videoprobe apparatus 10 in accordance with the present invention includes three primary subassemblies as shown in FIG. 1. The three primary subassemblies are a probe termination box 11, strong back 30, and videoprobe housing 50. The probe termination box 11 provides an interface with other equipment and the user. The preferred strong back 30 is an encasement in the shape of a hockey stick, and provides the mechanical support for the videoprobe housing 50 located at the curved portion 42 of the strong back 30. The strong back 30 provides protection for the connection components between the videoprobe housing 50 and the probe termination box 11. With reference also to FIG. 6, the videoprobe housing 50 contains an optics train 52, a CCD chip 60, and circuitry (electronics package) 62 to provide a signal to the probe termination box 11.

The probe termination box 11, as shown in FIG. 1, may be attached to the strong back 30 with screws or similar attachment devices 12. The probe termination box housing 13 in a preferred embodiment is made from Delrin nylon. The probe termination box 11 has two channels 14 connected to the strong back 30 for insertion of a sampler, nitrogen or other gas, or a fiberscope to conduct such through the strong back 30 and down to the videoprobe housing 50 for contact with an area being examined.

Figure 5:
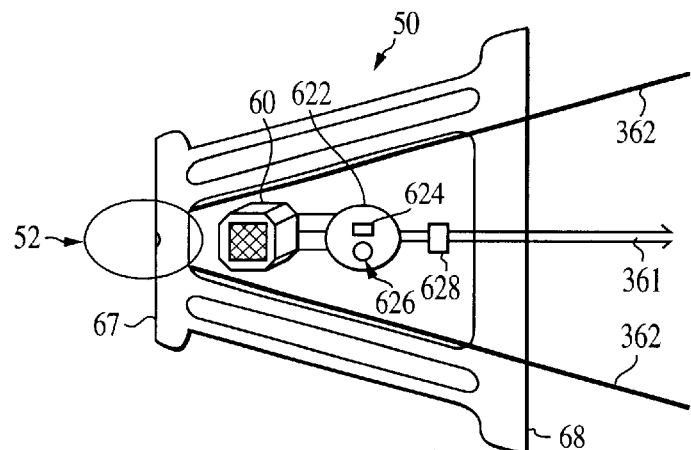
FIG. 5 is a schematic view of an isolated videoprobe in accordance with the present invention.

The probe termination box 11, as shown in FIG. 1, has a connection 16 for an umbilical cord 70 for universal attachment to well known video processors to process and display the image detected by the CCD chip. In a preferred form, the umbilical cord 70 is about 6 feet long and plugs into the standard Welch Allyn (a registered trademark of Welch Allyn, Inc.) VP-II or VP-III video processor 75 used with larger, commercially available, videoprobes. With reference also to FIG. 5, the umbilical cord 70 carries fiber bundle wires 362 and CCD image signal wiring 361.

The probe termination box 11 has two control levers 18 for controlling pusher bars 46 at the end of the strong back 30. These pusher bars 46 laterally deflect the videoprobe end of the strong back 30 by displacing the strong back 30 from any adjacent structure surfaces. This movement improves both video field adjustment and sampling capability. The control levers 18 pivot about connection point 182. Control cables 381 run from the control levers 18 to control the movement of the pusher bars 46.

Figure 2:
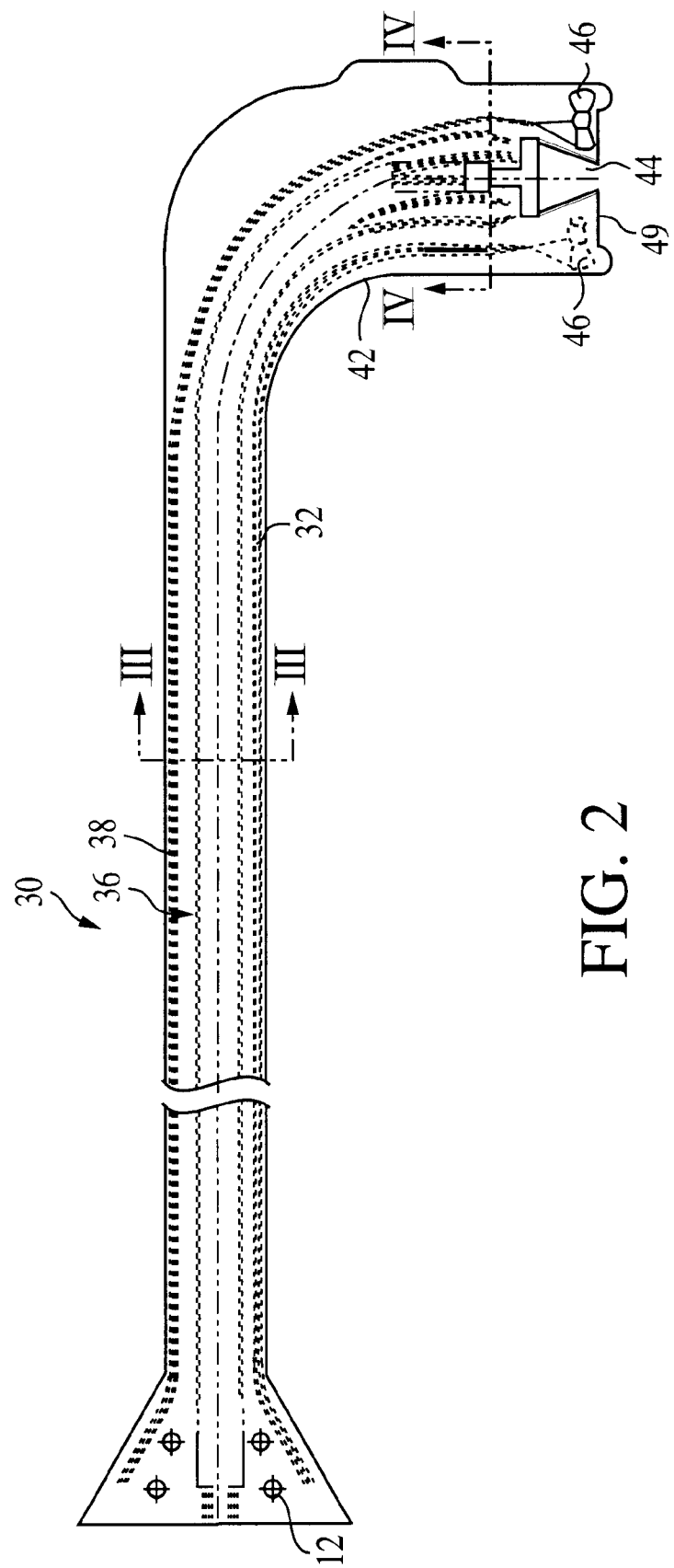
FIG. 2 is a view similar to FIG. 1 of the strong back of the videoprobe apparatus of FIG. 1.

Next, reference is made to the second subassembly, namely, the strong back 30 as shown in FIGS. 1 and 2. In the preferred embodiment, the strong back 30 is in the shape of a hockey stick and is made from Lexan plastic. In a contemplated embodiment, the hockey stick shape has an overall thickness of 0.125", a width of 2.5", and a nose length of 7". The length of the handle portion 32 of the hockey stick can be of any length while having a minimal effect on picture quality.

Figure 3:
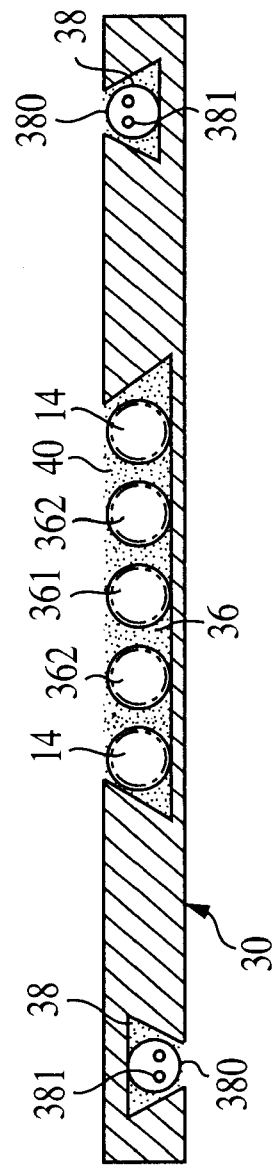
FIG. 3 is a cross-sectional view of the strong back taken at III—III of FIGS. 1 and 2.
Figure 4:
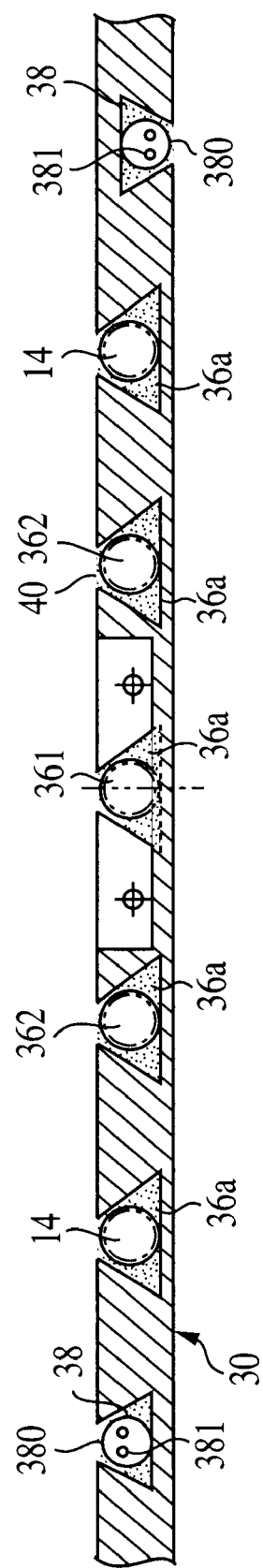
FIG. 4 is a cross-sectional view of the strong back taken at IV—IV of FIGS. 1 and 2.

Milled along its full length, the strong back 30 has a set of channels 36 and 38. Teflon (a registered trademark of E.I. DuPont De Nemours and Co.) tubes 14, 361, 362, and 380 are inserted and fixed into place in the milled channels 36, 36a, and 38 by epoxy 40 as shown in FIGS. 3 and 4. The milled channels 36 each may house more than one tube as shown in FIG. 3. In providing the strong back 30, it is preferred that the epoxy 40 flows evenly over the tubes 14, 361, 362, and 380 to create a surface that is even with the original thickness of the strong back 30. These tubes in turn carry the wiring for the CCD image signal 361, light guides for illumination 362, and may carry other items as desired. Other things that may be carried in these tubes are control cables 381 for the pusher bars 46, nitrogen for drying 14, and sampler tubes 14 for obtaining a physical sample from the area being viewed. In the nose 42 the main central channel 36 branches or fans-out into multiple channels 36a, each housing one tube 14, 361, and 362 as shown in FIGS. 1–4.

Figure 7:
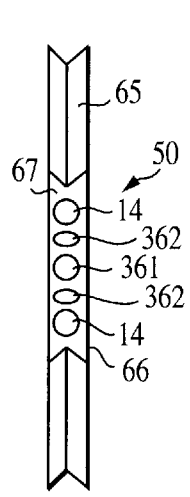
FIG. 7 is a front plan view of the videoprobe of FIG. 5.

The strong back 30 acts as a handle for placement of the videoprobe housing 50 to view a selected area. In the embodiment shown in FIG. 1, the strong back 30 is held together with the videoprobe housing 50 by pins 48. In addition, as shown in FIG. 7, the videoprobe housing has V-shape notches 65 along its edges to snap into the strong back 30 within a cavity 44. This connection minimizes the possibility of damage to the videoprobe. In contrast, it has been contemplated that most damage to fiberscopes occurs in the loading and removing of the fiberscope from the delivery tool.

Figure 8:
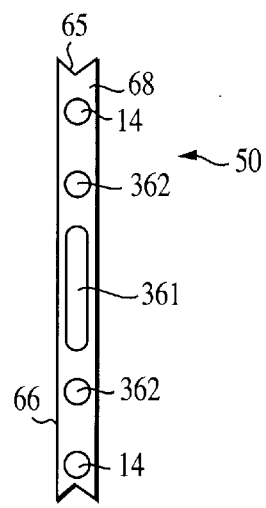
FIG. 8 is a rear plan view of the videoprobe of FIG. 5.

The videoprobe housing 50 has an overall minor dimension (head height) of 0.110". The preferred embodiment of the videoprobe housing 50 has the following approximate dimensions: 7/16" for the front major dimension (head front 67 as shown in FIG. 7), 1 and 3/16" for the rear major dimension (head back 68 as shown in FIG. 8), and 1" for the head length. These dimensions provide the videoprobe housing 50 with an arrowhead shape as shown in FIG. 5.

As shown in FIGS. 7 and 8, videoprobe housing 50 is formed by sandwiching the internal components between two thin steel plates 66, which protect and provide support to prevent damage to the device and the imaging components. Preferably, the two steel plates 66 are epoxied together to provide a water tight seal thus protecting the imaging components from water damage. The steel plates 66 provide stability and protection to the optics train located at the leading edge 49 of the hockey stick configuration.

The videoprobe also includes an optics train 52 and imagery circuitry 60 and 62 all in alignment along a longitudinal axis A—A as shown in FIG. 6. The preferred embodiment for the optics train 52 receives light through a window 522 formed by quartz glass. Light passes through a 0.006" drilled aperture 524 and is focused onto the CCD chip 60 through a focusing lens 526 made of focusing glass. The focusing lens 526 automatically focuses on an object from approximately 4 mm to infinity. In the shown embodiment, the optimal focusing distance is 10 mm.

Image circuitry receiving light from the object in view includes the CCD chip 60 and an electronics package 62 to operate the videoprobe and output an electrical image signal into the fiber optics in tube 361 as shown in FIGS. 5–6. The CCD chip 60 utilized in development of an implemental embodiment was a Texas Instrument (a registered trademark of Texas Instruments Inc.) TC227. Such a CCD 60 chip provides a resolution of approximately 10,000 pixels per fiber bundle. The electronics package 62 is located behind the CCD chip 60 in an area of the videoprobe housing arrowhead shape where there is ample room as shown in FIG. 5. This arrangement allows for the minor distance of the videoprobe housing to be approximately 0.110". The electronics package 62 includes a hybrid circuit board 622 connected in series with a capacitor 628. The hybrid circuit board 622 includes a transistor 624 and resistor 626. Electronics package 62 uses known components for the components 624, 626, and 628 thereof.

Light to be reflected by the object being viewed is provided by the light guides 362 as shown in FIG. 5. By operating the light in a strobe mode, the output black and white CCD chip can create a composite color image. However, a normal non-strobe mode will provide a standard black and white picture, which is more useful when trying to view objects that are more distant.

Auxiliary tubes 14 in the strong back 30 have corresponding tubes within the videoprobe housing 50 as shown in FIGS. 7 and 8. Consequently, anything inserted in the probe termination box 11 and sent through the strong back 30 will reach the videoprobe housing 50 and be capable of interacting or retrieving data or samples for transmission back to the probe termination box 11.

The special structure of this invention allows it to operate in a 0.110" restricted space at up to 90 percent humidity and 110 degrees Fahrenheit. Furthermore, the present invention increases the efficiency of steam generator secondary side inner tube bundle inspection by approximately sevenfold. The fixed connection of the videoprobe housing 50 and the strong back 30 allows for a permanent view orientation which translates into quicker access of target locations and better accuracy in obtaining the correct target.

The videoprobe 50 can be inserted as a stand-alone apparatus into a delivery tool, like the above-discussed hockey stick configuration, and then removed upon completion of the inspection. This repackaging would increase the portability of the tools and flexibility of the videoprobes. The light guides 362 could be incorporated with the videoprobe or be a part of the delivery tool. The videoprobe 50 relies on a sheath design to allow it to easily connect and disconnect from a delivery tool.

While the presently preferred embodiments of the present invention have been shown and described, it is to be understood that this disclosure is for the purpose of illustration and that various changes and modifications may be made without departing from the scope of the invention as set forth in the appended claims.

We claim:

1. A videoprobe apparatus for use in restricted spaces, comprising:

a probe termination box;

a strong back connected to said probe termination box; and a videoprobe having a housing attached to said strong back, an optics train, a CCD chip, and an electronics package, wherein said optics train, said CCD chip, and said electronics package are in alignment within said housing along a longitudinal axis, and wherein said optics train includes a window, an aperture, and a lens spaced from one another to provide reflected light from an object to said CCD chip, and wherein two thin plates sandwich said internal components of said videoprobe housing, said two thin plates providing an overall minor dimension of not greater than approximately 0.110", and said aperture having an opening of about 0.006" for reflected light to pass through to said lens and be focused upon said CCD chip.

2. The videoprobe apparatus as recited in claim 1, wherein said two thin plates are epoxied together to provide a watertight seal and are formed of steel.

3. The videoprobe apparatus as recited in claim 1, wherein said strong back has a hockey stick shape.

4. The videoprobe apparatus as recited in claim 1, wherein said videoprobe housing has V-shape notches along the sides to facilitate attachment to the bottom of said strong back.

5. A videoprobe for connection to a delivery tool comprising:

a housing;

an optics train including optical elements aligned along a longitudinal axis through said housing;

a CCD chip; and an electronics package, wherein said CCD chip, and said electronics package also are aligned with said optical elements along said longitudinal axis, and wherein two thin plates sandwich said internal components of said videoprobe housing, said two thin plates providing an overall minor dimension of not greater than approximately 0.110", and said aperture has an opening of about 0.006" for reflected light to pass through to said lens and be focused upon said CCD chip.

6. The videoprobe as recited in claim 5, wherein said two thin plates are epoxied together to provide a watertight seal and are formed of steel.

7. The videoprobe as recited in claim 5, wherein said optical elements include a window, an aperture, and a lens spaced form one another to provide reflected light from an object to said CCD chip.

8. The videoprobe as recited in claim 5, wherein said electronics package includes a hybrid circuit board in series with a capacitor.

9. The videoprobe as recited in claim 5, wherein said videoprobe housing has V-Shape notches along the sides to facilitate attachment to a delivery tool.

* * * * *